US008361099B2

(12) United States Patent
Schosnig et al.

(10) Patent No.: US 8,361,099 B2
(45) Date of Patent: Jan. 29, 2013

(54) PUNCTURE AID WITH PROTECTION AGAINST REUSE

(75) Inventors: Stefan Schosnig, Hirschberg-Großsachsen (DE); Wolfgang Handel, Mannheim (DE); Wolfgang Jost, Boebingen (DE); Lydia Kolonko, Heppenheim (DE); Hans List, Hesseneck-Kailbach (DE); Jack Griffis, Decatur, GA (US); Brian Leutz, Suwannee, GA (US); Jeff Stout, Smyrna, GA (US); Gwenn Kennedy, Ellenwood, GA (US); Bradley Koeppel, Smyrna, GA (US); Jeff Noble, McDonoveh, GA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1098 days.

(21) Appl. No.: 11/621,633

(22) Filed: Jan. 10, 2007

(65) Prior Publication Data
US 2007/0185516 A1    Aug. 9, 2007

(30) Foreign Application Priority Data

Jan. 10, 2006  (EP) .................................. 06100216

(51) Int. Cl.
A61B 17/14    (2006.01)
A61B 17/32    (2006.01)

(52) U.S. Cl. .......................... 606/181; 606/182; 606/167

(58) Field of Classification Search .................. 606/181, 606/182, 183, 185, 186, 167, 187; 600/583, 600/573, 565; 604/117, 207–211
See application file for complete search history.

(56) References Cited

U.S. PATENT DOCUMENTS

| 4,527,561 A | 7/1985 | Burns |
| 6,514,270 B1 | 2/2003 | Schraga |

(Continued)

FOREIGN PATENT DOCUMENTS

| EP | 1 371 329 | 12/2003 |
| JP | 2003-512883 | 4/2003 |

(Continued)

OTHER PUBLICATIONS

Office Action, Japanese patent application No. 348507/2006; dated Jun. 15, 2010.

Primary Examiner — Ryan Severson
Assistant Examiner — Tin Nguyen
(74) Attorney, Agent, or Firm — Bose McKinney & Evans LLP

(57) ABSTRACT

The present invention provides a puncture aid comprising a housing in which a lancet holder with a lancet is displaceably mounted, the lancet holder being connected to a spring element. The lancet holder has at least one bearing element and the housing has a support surface arranged such that the bearing element rests on the support surface in a first position of the lancet holder. A trigger unit is provided, actuation of which transfer the lancet holder to a second position by means of a relative rotational movement of the bearing element and the support surface, so that the bearing element falls from the support surface in the second position of the lancet holder, and the tensioned spring element at least partially relaxes and moves the lancet holder such that the tip of the lancet emerges from the opening of the housing. The puncture aid includes a blocking element which is arranged such that it blocks a relative rotational movement of the bearing element and the support surface with respect to one another after the trigger unit has transferred the lancet holder to the second position with the result that reuse of the puncture aid is prevented.

37 Claims, 8 Drawing Sheets

U.S. PATENT DOCUMENTS

| | | | |
|---|---|---|---|
| 6,719,771 B1 | 4/2004 | Crossman | |
| 6,764,496 B2 | 7/2004 | Schraga | |
| 7,238,192 B2 * | 7/2007 | List et al. | 606/182 |
| 2003/0216767 A1 * | 11/2003 | List et al. | 606/181 |
| 2005/0288699 A1 * | 12/2005 | Schraga | 606/181 |

FOREIGN PATENT DOCUMENTS

| | | |
|---|---|---|
| JP | 2003-325484 | 11/2003 |
| WO | WO 01/32086 A1 | 5/2001 |
| WO | WO 2004/039429 A2 | 5/2004 |

* cited by examiner

PUNCTURE AID WITH PROTECTION AGAINST REUSE

RELATED APPLICATIONS

This application claims priority to EP 06100216.8, filed Jan. 10, 2006.

BACKGROUND

The present invention relates to a disposable puncture aid, and in particular, a disposable puncture aid whose reuse is prevented by a blocking element.

Samples of body fluids, in particular, blood, are taken with the aim of carrying out a subsequent analysis, in order to permit diagnosis of diseases or to monitor the metabolic status of a patient. Such samples are taken by diabetics, in particular, for determining blood sugar concentration. In order to collect only small quantities of blood for diagnostic purposes, sterile, sharp lancets are normally used which, for example, are briefly inserted by hospital staff or by the patients themselves into the finger pad or into other parts of the body. In the area of home monitoring in particular, where persons without specialized medical training carry out simple analyses of blood themselves, lancets and associated devices (blood sampling devices, blood lancet devices or, as they are referred to in the following description, "puncture aids") are sold which allow samples of blood to be taken with the least possible discomfort and in a reproducible manner.

Disposable puncture aids that include a mechanism to prevent multiple use are known in the prior art. Allowing multiple use of a puncture aid introduces a risk of the user being contaminated or infected by blood residue present on the lancet of the puncture aid.

U.S. Pat. Nos. 6,764,496 and 6,514,270 each relate to a disposable lancet device for single use, with a lancet which is arranged in the interior of a housing and which is movable between a tensioned position and a puncture position. A restrictor assembly is designed such that it engages the lancet and ensures that, after movement into the puncture position, the lancet cannot be moved back again to the tensioned position.

U.S. Pat. No. 6,719,771 relates to a blood sampling device that includes a sleeve with a spring-loaded lancet which can be released from a tensioned, rearward position by means of a trigger mechanism, in order to allow its tip to project instantaneously from the forward end of the sleeve. The lancet has a deflectable or releasable attachment which can be engaged with the sleeve and which holds the lancet counter to the pressure of the spring, the attachment extending rearward from the lancet and engaging behind a projection which is provided on an inner structure of the sleeve. The lancet is released by the trigger, which is formed integrally with the sleeve and is pressed transversely with respect to the sleeve, which unlocks the attachment. Moreover, when activated, the trigger can enter into a snap-fit engagement with the sleeve in order to retain the latter in its activated position.

The subject matter of EP 1 371 329 A1 (and corresponding U.S. patent application Ser. No. 10/437,717) is a puncture aid comprising a housing which has an opening and in which a lancet holder with a lancet is displaceably mounted. The lancet holder is connected to a spring element and includes at least one bearing element. At least one support surface is arranged in the housing in such a way that the bearing element rests on the support surface in a first position of the lancet holder. The puncture aid also comprises a trigger unit by means of which the lancet holder is transferred to a second position, a trigger button of the trigger unit executing a linear movement, and the linear movement being converted into a relative movement of the bearing element and the support surface with respect to one another. In the second position of the lancet holder, the bearing element falls from the support surface, and the spring element, tensioned prior to the falling movement, at least partially relaxes and moves the lancet holder relative to the housing, so that the tip of the lancet emerges from the opening of the housing.

This puncture aid according to EP 1 371 329 A1 has the disadvantage that, by using a suitable tool in the form of an elongate element that can be inserted through the opening into the housing, the bearing element can be returned to the support surface by means of a linear movement and a subsequent rotation movement. Depending on the design of the sterile protector, the latter itself can even serve as a tool for renewed tensioning of the puncture aid. Undesired reuse of the puncture aid is therefore possible. EP 1371 329 A1 proposes a system of protection against reuse in which, after the puncture process, the bearing element is pressed upward by a spring element against the support surface. However, even with such a system of protection against reuse, renewed tensioning of the puncture aid by using a tool cannot be prevented.

SUMMARY OF THE INVENTION

The present invention provides a system to prevent reuse of a puncture aid. According to exemplary embodiments, the puncture aid comprises a housing which has an opening and in which a lancet holder with a lancet is displaceably mounted, the lancet holder being connected to a spring element, and the lancet holder having at least one bearing element, and in which housing at least one support surface is arranged in such a way that the bearing element rests on the support surface in a first position of the lancet holder. A trigger unit is provided by means of which the lancet holder, through actuation of a trigger button, is transferred to a second position by means of a relative rotation or movement of the bearing element and the support surface with respect to one another, so that the bearing element falls or is released from the support surface in the second position of the lancet holder, in which process the spring element, tensioned prior to the falling movement, at least partially relaxes and moves the lancet holder relative to the housing, such that the tip of the lancet emerges from the opening of the housing. The puncture aid includes a blocking element which is arranged in such a way that it blocks a relative rotational movement of the bearing element and the support surface with respect to one another after the trigger unit has transferred the lancet holder to the second position through the relative rotational movement of the bearing element and the support surface with respect to one another, with the result that reuse of the puncture aid is prevented.

As regards the structure of the puncture aid and its mode of operation, except for the system of protection against reuse, reference is expressly made to document EP 1 371 329 A1 (U.S. patent application Ser. No. 10/437,717).

In one embodiment, the puncture aid additionally has a blocking element which, after the puncturing process, blocks a relative rotation of the bearing element and of the support surface with respect to one another. This blocking action prevents the puncture aid from being reused after its first use.

The blocking element may be configured to automatically block a relative rotation of the bearing element and of the support surface with respect to one another after the trigger unit has transferred the lancet holder to the second position through the relative rotation movement of the bearing element and the support surface with respect to one another. However, the blocking element may also be configured such that a maneuver on the part of the user is required in order to obtain the blocking of the rotation by the blocking element.

The blocking element may be arranged in such a way that, after the puncture movement has been triggered, it either blocks a rotation of the bearing element relative to the support surface back to the first position or blocks a renewed rotation of the bearing element relative to the support surface from the first position to the second position. In the first case, the blocking action by the blocking element prevents renewed tensioning of the puncture aid by rotation of the bearing element back onto the support surface. In the second case, renewed tensioning of the puncture aid is possible, if appropriate, but the latter cannot then be triggered again, because the blocking element prevents the bearing element from being turned away from the support surface again and from falling from the latter.

In one embodiment, the trigger button belonging to the trigger unit executes a substantially linear movement when actuated, and this linear movement is converted to a relative rotation of the bearing element and of the support surface with respect to one another. The blocking element is in this case arranged in such a way that it blocks a relative rotation of the bearing element and of the support surface with respect to one another after the trigger button has executed the linear movement for triggering a puncture movement of the lancet.

In one embodiment, the trigger unit contains at least one rotary drive element which is pressed against the at least one bearing element by means of the linear movement of the trigger button and in this way effects a rotation of the bearing element relative to the support surface, the trigger button having at least one hook which is arranged in such a way that, after the linear movement of the trigger button, it catches in the housing, so that the trigger button cannot execute a linear return movement, and the rotary drive element remains arranged in such a way that it acts as blocking element and blocks a rotational movement of the bearing element relative to the support surface back to the first position. The rotary drive element is pressed against the bearing element by the linear movement of the trigger button and it displaces this bearing element from the support surface, such that the lancet executes the puncture movement. The trigger button is then hooked in a pressed-in position by the hook, so that it cannot move back in a linear return movement to its starting position before the triggering of the puncture aid. It is hooked in a position in which the rotary drive element is still arranged on the support surface from which it has displaced the bearing element, and therefore blocks a reverse rotation of the bearing element to the first position.

In one embodiment, the lancet holder has two bearing elements which, in the first position, each rest on a support surface of the housing. In this case, the trigger button preferably has two rotary drive elements. However, any desired number of bearing elements and associated support surfaces and rotary drive elements is possible.

In one embodiment, after the linear movement of the trigger button, the hook hooks into a recess of the housing or behind a projection of the housing. During the linear movement of the trigger button, the hook can, for example, slide over a ramp-shaped projection of the housing and, after the linear movement, can hook in behind the ramp-shaped projection. Moreover, before the puncture movement of the lancet is triggered, the hook can hook the trigger button to the housing in another position in order to prevent detachment of the trigger button from the housing before the puncturing process is triggered. For this purpose, two projections can be provided in the housing for example, these projections being arranged in such a way that, before a puncturing process is triggered, the hook is hooked in behind the first projection and the trigger button cannot therefore be detached from the housing, and, after the linear movement of the trigger button, it is hooked in behind the second projection, so that the blocking element (rotary drive element) blocks the support surface. For this purpose, however, the trigger button can also have at least two hooks, at least one hook serving to hook the trigger button in the housing before the puncture movement is triggered, and at least one further hook serving to hook the trigger button in the housing after the linear movement, so as to prevent the linear return movement of the trigger button.

In one embodiment, the puncture aid has a detachable sterile protector with projections which are arranged in such a way that, after the puncture movement of the lancet, the sterile protector can be inserted as a blocking element into the opening of the housing of the puncture aid and hooks itself with its projections in the opening and blocks the opening of the housing, such that a rotational movement of the bearing element relative to the support surface is prevented by the sterile protector.

At the time of delivery, the puncture aid according to exemplary embodiments is in a tensioned state, and a sterile protector is pushed over the lancet in order to ensure the sterility of the lancet before its use and in order to avoid accidental injuries caused by the lancet. The sterile protector can be removed prior to the use of the puncture aid. After said use, the sterile protector can serve as a blocking element by means of the user inserting it back into the housing via the opening (preferably in the reverse direction in relation to its removal), and during the process, it hooks itself in the opening by means of its projections and thereby prevents a rotation movement of the bearing element relative to the support surface and, consequently, prevents reuse of the puncture aid.

The sterile protector of the puncture aid according to the invention may be designed in such a way that, after detachment from the lancet, it cannot be moved back in and out of the housing via the opening through which the lancet tip emerges during the puncturing process, so that the sterile protector is not suitable as a tool for renewed tensioning of the puncture aid after a puncturing process. For this purpose, the sterile protector can have at least one portion that has a diameter greater than the opening of the housing and prevents insertion of the sterile protector into the opening or prevents withdrawal of a sterile protector that has been inserted into the opening. In the latter case, the portion with the greater diameter can lock in the opening as soon as it has been inserted into the opening.

In one embodiment, the puncture aid comprises, as blocking element, a switch element which is designed to be movable in one direction in order to allow the lancet holder to pass during a relative rotation of the bearing element and the support surface with respect to one another, and, in another direction, is movable only as far as a blocking position, which switch element blocks the lancet holder in the blocking position in such a way that it prevents a rotational movement back to the first position. The switch element can thus be moved aside, in particular folded aside or bent aside, in one direction, so that it does not obstruct the lancet holder upon triggering of the puncturing process, with the result that the lancet holder is able to execute the puncturing movement. In the other direction, the blocking element can be moved as far as a blocking position and, in this position, after the puncturing process, it counteracts a reverse rotation of the lancet holder to the starting position that is assumed before the puncturing process was triggered. It thus blocks a rotation movement for renewed tensioning of the puncture aid.

The switch element can be arranged at the edge of the support surface or on the lancet holder. The edge of the support surface signifies that edge across which the bearing element moves upon rotation from the first position to the second position, immediately before the lancet holder executes the falling movement. Adjacent to this edge, there is preferably a guide groove which extends along the opening in the housing and in which the bearing element is guided during a linear falling movement in the puncturing process.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein.

Corresponding reference numerals are used to indicate corresponding parts throughout the several views.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
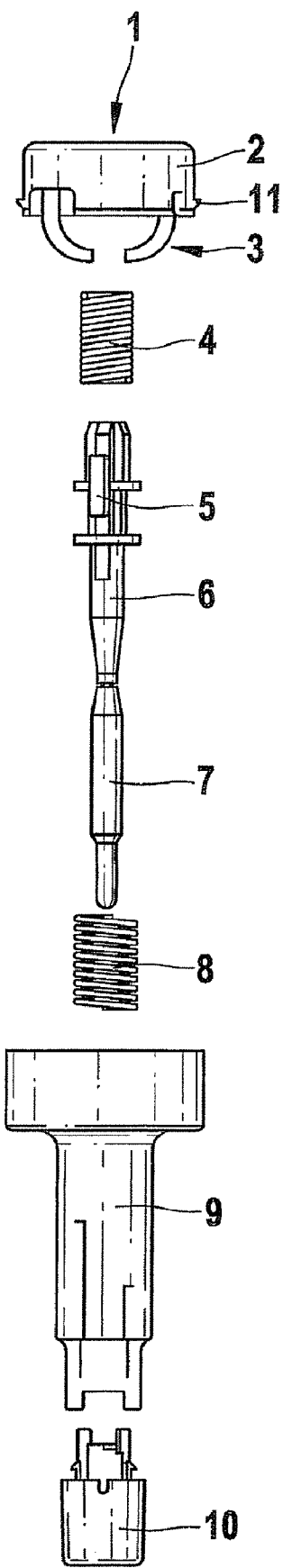
FIG. 1 is an exploded plan view of the components that are assembled to form a puncture aid.

FIG. 1 shows component parts of the puncture aid before they have been assembled. The puncture aid has a housing 9 into which the lancet holder 6 is inserted. The lancet holder 6 is movably or displacably mounted in the housing such that it can be guided along the puncturing direction during a puncturing procedure. For this purpose, the system also includes drive elements which are connected to the lancet holder 6 and act on the latter. In the example shown, the drive elements are in each case in the form of a spring (4 and 8). In this connection, as shown in FIG. 1, the lancet holder 6 can rest loosely on a spring element or abut the latter, without a fixed connection between the spring element and lancet holder 6. Within the meaning of this disclosure, the connection between the lancet holder 6 and a drive element is characterized in that a force can be transmitted from the drive element to the lancet holder 6. However, embodiments are also possible in which the lancet holder 6 is fixedly connected to a drive element. The lancet holder 6 is also positioned in the housing 9 in such a way that it can execute a rotation substantially perpendicular to the puncturing direction. The lancet holder 6 itself has a sterile protector 7 which is pushed over a lancet in order to ensure the sterility of the lancet before use thereof and to prevent accidental injury by the lancet tip. The spring 8 is first inserted into the housing 9. During subsequent use of the puncture aid, this prevents the lancet from being conveyed back into the housing after the lancing process. The spring 8 is also referred to as a return spring. The lancet holder 6 is inserted inside the spring 8 and the housing. The lancet holder 6 is also provided with bearing elements 5 which rest within the housing on support surfaces 20 (See FIG. 2) provided for this purpose. The spring 4 and the spring 8 both interact with the lancet holder 6 in such a way that, when the bearing elements 5 rest on the support surfaces 20 within the housing 9, the spring 4 (drive spring) is tensioned, while the spring 8 (return spring) is relaxed. During the puncturing process, the drive spring 4 relaxes as it accelerates the lancet holder 6. The latter executes a falling or puncture movement and strikes the return spring 8, which is thereby tensioned. The lancet holder 6 falls or moves within the housing down to a limit stop. The lancet holder 6 is then pulled back again by the return spring 8 which is then fully tensioned. At this time the drive spring 4 is relaxed. A cap 10 is movably mounted on the lower end of the housing 9, so that, by a rotational movement of the cap, the length of the part of the lancet tip emerging from the housing can be changed. Different puncture depths of the lancet can be set by means of this adjustable distance of the cap 10. At the upper end of the housing, the trigger or trigger unit 1 closes the upper opening of the housing. In the example shown, the trigger unit comprises a trigger button 2 and two small elastic hooks 3 as rotary drive elements. When the button 2 is actuated along the lancing direction of the lancet, the small hooks 3 cause a rotational movement of the lancet holder 6.

The trigger button 2 has two hooks 11 with which the trigger button 2 catches in the housing 9, so that, in the assembled state of the puncture aid, it cannot fall from or be detached from this. According to one embodiment, after the trigger has been pressed to trigger a puncture process (after the linear movement of the trigger button 2), these hooks can catch on the housing so that the trigger button 2 cannot execute a linear return movement to the starting position and the rotary drive elements 3 remain arranged in such a way that they act as blocking elements to block a rotation movement of the bearing elements 5 relative to the support surfaces 20 back to the first position. This particular embodiment is explained in more detail with reference to FIGS. 3A, 3B, 4A and 4B.

Figure 2:
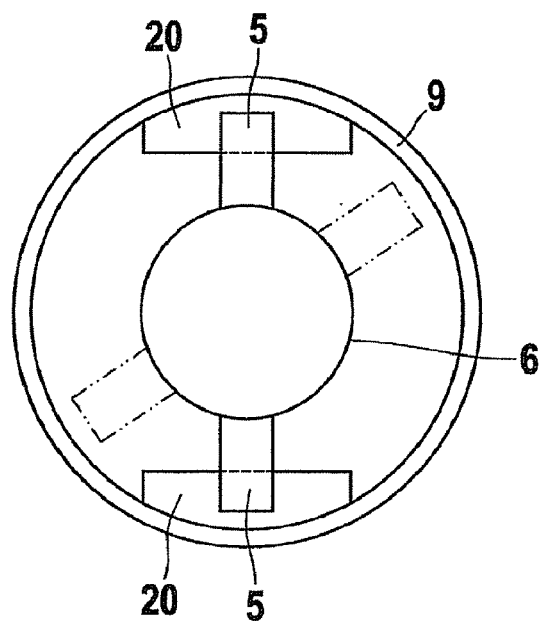
FIG. 2 is a plan view of the lancet holder of a puncture aid according to FIG. 1, arranged inside the housing.

FIG. 2 shows a plan view of the puncture aid according to FIG. 1, where the lancet holder 6 is located in a first position in the lancet housing 9. In the example shown, the lancet holder 6 has two bearing elements 5 which are designed in the form of holding arms. In the first position, the holding arms 5 rest on the support surfaces 20 of the housing 9. By means of a rotational movement of the lancet holder 6, the bearing elements 5 are moved to a second position (shown in phantom) in which they no longer rest on the support surfaces. The lancet holder connected to the bearing elements can now execute a movement in the puncturing direction. A puncture process is carried out by the movement of the lancet holder in the puncturing direction.

Figure 3A:
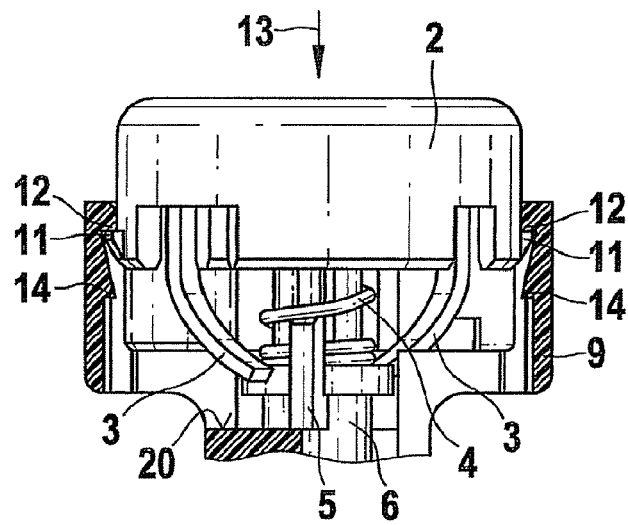
FIG. 3A is a sectional detail of a first embodiment of a puncture aid before its first use.

FIG. 3A shows a sectional detail of a first embodiment of a puncture aid before the first use. The trigger is shown with its two hooks 11. Before use of the puncture aid, the hooks 11 are hooked behind two upper projections 12 of the housing 9, so that the trigger is locked in the housing 9 above lower projections 14 of the housing 9. Small hooks 3 acting as rotary drive elements are connected to the trigger button 2. In the illustrated position of the trigger button 2 (not pressed down), the small hooks 3 are spaced apart from the bearing elements 5 of the lancet holder 6, which in the first position rest on the support surfaces 20 (not shown). The drive spring 4 is in a tensioned (compressed) state. When the trigger button 2 is pressed in the axial direction 13, the trigger button 2 executes a linear movement in the axial direction. In this way, the rotary drive elements 3 are pressed against the bearing elements 5, which consequently execute a rotation movement relative to the support surfaces 20. The lancet holder 6 is rotated until the bearing elements 5 fall from the support surfaces 20. The lancet holder 6 including the lancet is then accelerated by the drive spring 4 in the axial direction 13 and executes a puncturing movement.

Figure 3B:
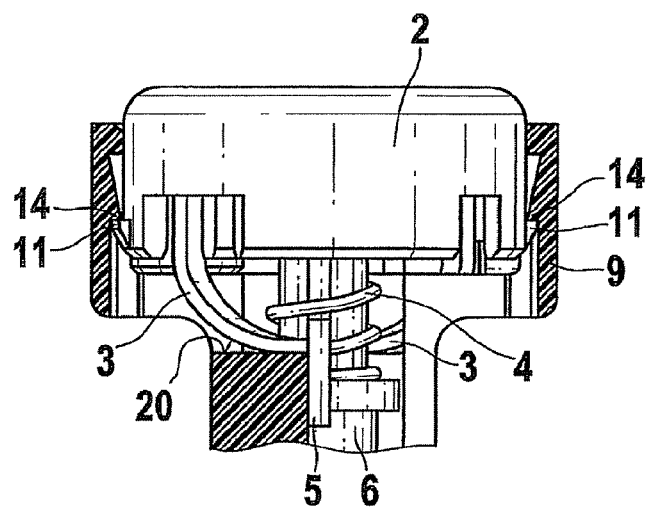
FIG. 3B is a sectional detail of the puncture aid according to FIG. 3A, after the first use.

FIG. 3B shows a sectional detail of a puncture aid as depicted in FIG. 3A, after the first use. By pressing the trigger button 2, the latter has been lowered in the housing 9. The hooks 11 have hooked in behind the lower projections 14 in the housing 9, such that the trigger button 2 cannot execute a linear return movement to its starting position according to FIG. 3A. In the hooked position of the trigger button 2 shown in FIG. 3B, the rotary drive elements 3 rest on the support surfaces 20, from which they have displaced the bearing elements 5 when the puncture aid was triggered. The rotary drive elements 3 therefore serve as blocking elements which prevent a rotational movement of the bearing elements 5 onto the support surfaces 20.

In the embodiment of a puncture aid according to the invention depicted in FIGS. 3A and 3B, the lower projections 14 are designed as ramp-shaped projections over which the hooks 11 slide during the linear movement of the trigger button 2 in the axial direction 13, until they hook in behind the lower projections 14, as shown in FIG. 3B.

Figure 4A:
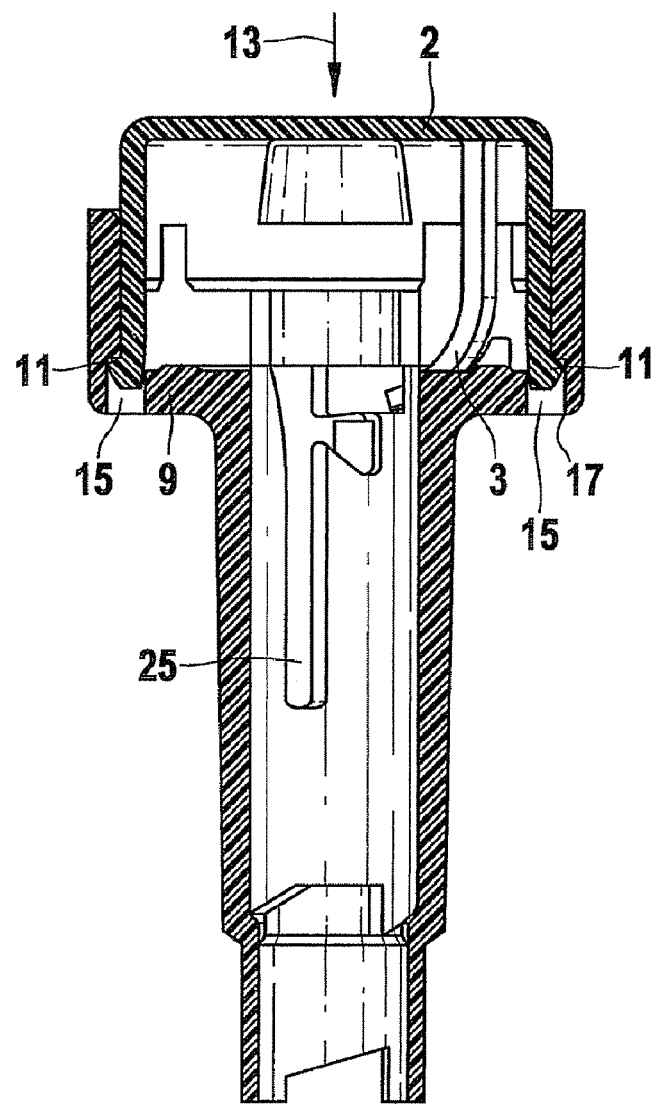
FIG. 4A shows a second embodiment of a puncture aid before its first use.

FIG. 4A shows a second embodiment of a puncture aid before its use. The trigger button 2 of this puncture aid has two hooks 11 which hook the trigger button 2 in each case in a recess 15 of the housing 9, so that the trigger button 2 cannot be detached from the housing 9. In the puncture aid shown in FIG. 4A, the bearing elements 5 of the lancet holder 6 rest on the support surfaces 20 (not shown), and the rotary drive elements 3 (small hooks) are spaced apart from the bearing elements 5.

Figure 4B:
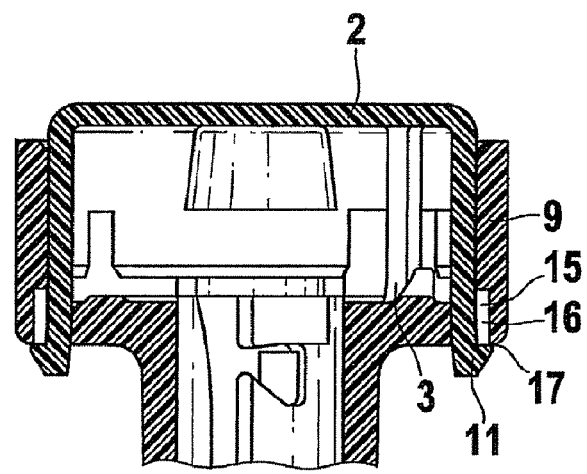
FIG. 4B is a sectional detail of the puncture aid according to FIG. 4A, after the first use.

When the trigger button 2 is pressed down in order to trigger a puncturing process, the bearing elements 5 are displaced from the support surfaces 20 by the rotary drive elements 3 and fall into the guide grooves 25. The hooks 11 each slide through a housing opening 16 until they emerge from the housing 9 and hook in behind an edge 17 on the outside of the housing 9. This hooked position is shown in FIG. 4B. The rotary drive elements 3 are positioned on the support surfaces 20 (not shown), so that they serve as blocking elements that do not permit rotation of the bearing elements back onto the support surfaces.

Figure 5A:
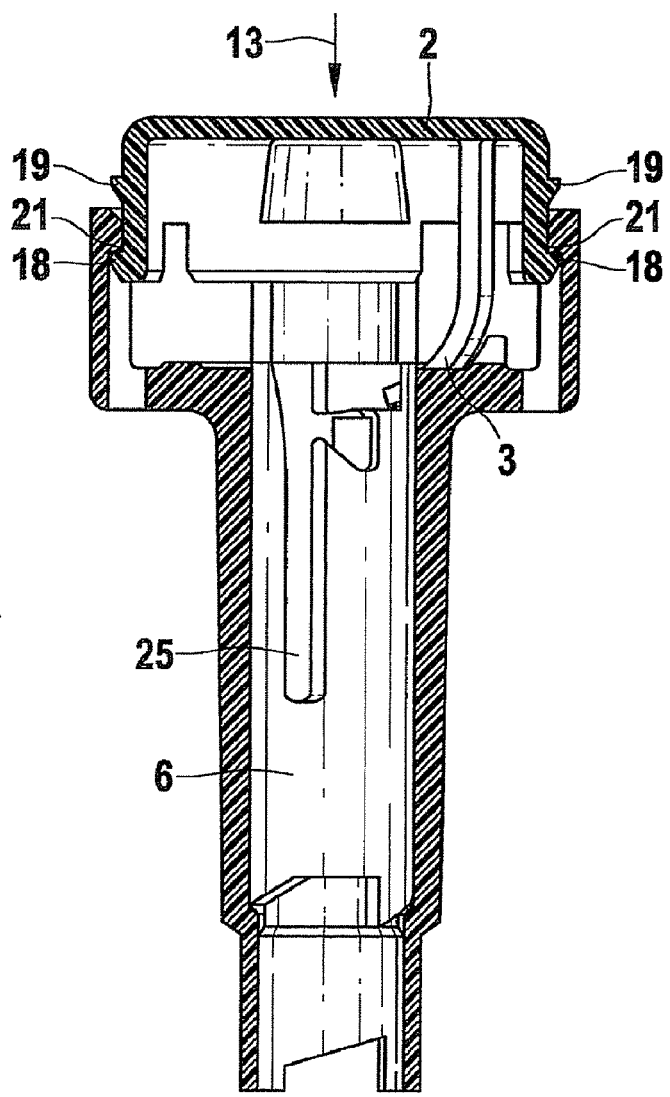
FIG. 5A shows a third embodiment of a puncture aid before its first use.

FIG. 5A shows a third embodiment of an unused puncture aid. The trigger button 2 of this puncture aid has four hooks, namely two lower hooks 18 and two upper hooks 19. In the position shown in FIG. 5A, the lower hooks 18 are hooked in behind projections 21 on the upper edge of the housing 9, so that the trigger button 2 is held securely on the housing. The rotary drive elements 3 designed as small hooks are arranged spaced apart from the bearing elements 5 that rest on the support surfaces 20 (not shown).

Figure 5B:
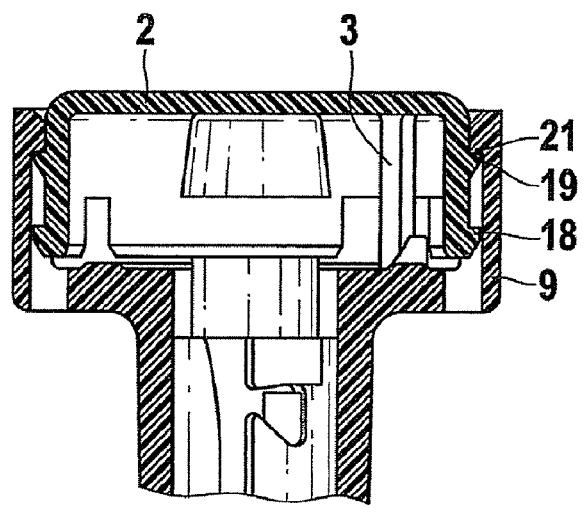
FIG. 5B shows a sectional detail of the puncture aid according to FIG. 5A, after the first use.

By pressing the trigger button 2 down, the latter is displaced linearly in the axial direction 13. The rotary drive elements 3 are pressed against the bearing elements 5, so that the lancet holder 6 executes a rotation movement and the bearing elements 5 fall from the support surfaces 20 (not shown) into the guide grooves 25. The lancet then executes a puncturing movement. As is shown in FIG. 5B, the trigger button 2 is hooked with the upper hook 19 behind the projections 21 after the linear movement in the housing 9, in order to prevent a linear return movement of the trigger button 2 to its starting position. In this position, the rotary drive elements 3 (blocking elements) block the support surfaces 20, so that a return rotation of the bearing elements 5 onto the support surfaces 20 is prevented. The puncture aid is therefore not reusable.

It is also possible to provide different projections in the housing 9 for the lower hooks 18 and the upper hooks 19, in which case the hooks 18, 19 are not arranged directly above one another on the trigger button 2, but instead offset about the circumference of the trigger button 2, on the outside of the trigger button 2.

Figure 6A:
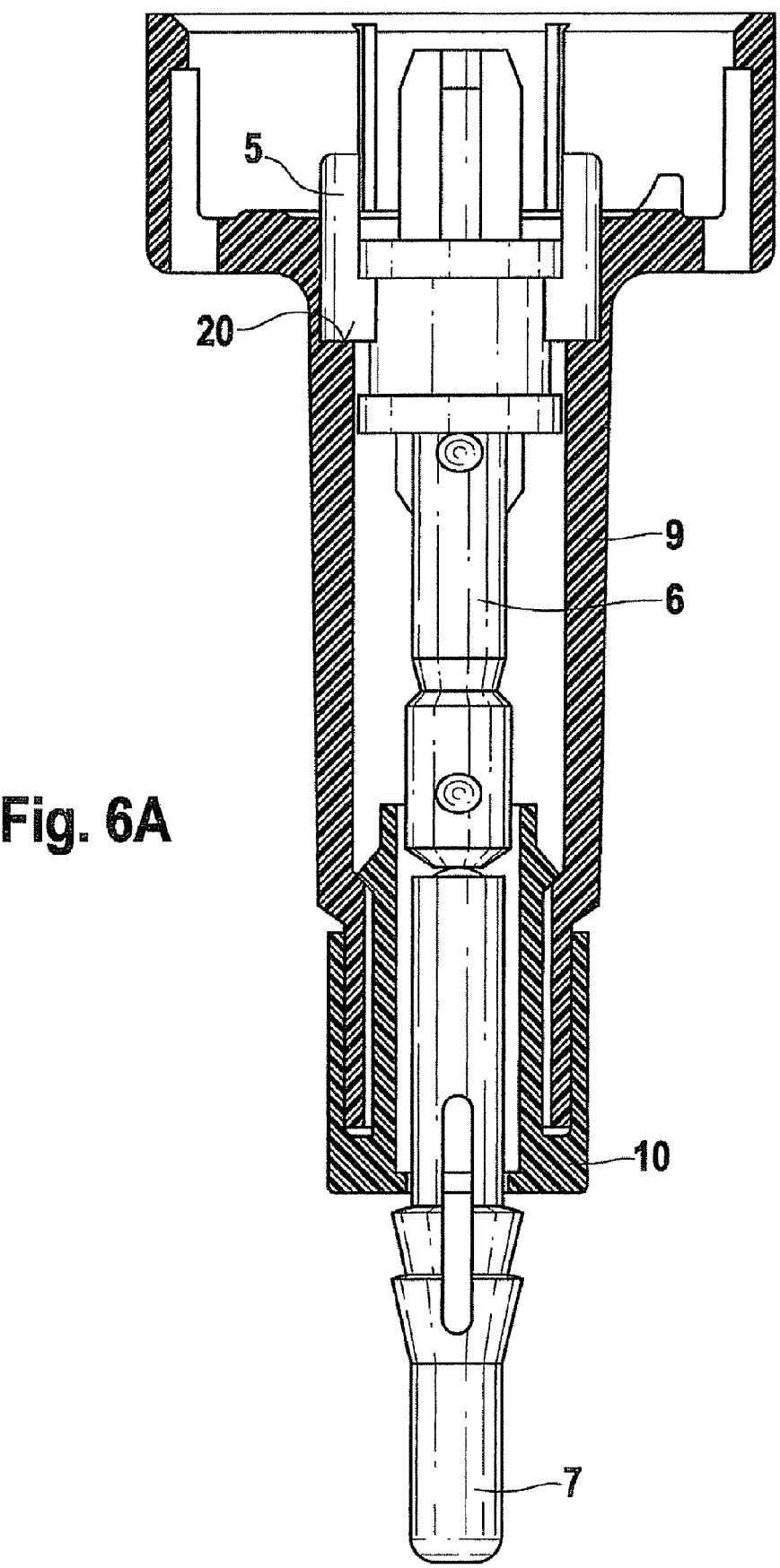
FIG. 6A shows a fourth embodiment of a puncture aid before its first use.

FIG. 6A shows a fourth embodiment of a puncture aid before its first use. The puncture aid has a sterile protector 7 which can be used as a blocking element and which, before the first use of the puncture aid, is pushed over a lancet so as to be removable therefrom and bears with one end on the lancet holder 6. Otherwise, the puncture aid is preferably as described in EP 1 371 329 A1 and comprises a trigger button 2, a housing 9 with support surface 20, and a lancet holder 6 with bearing element 5.

Figure 6B:
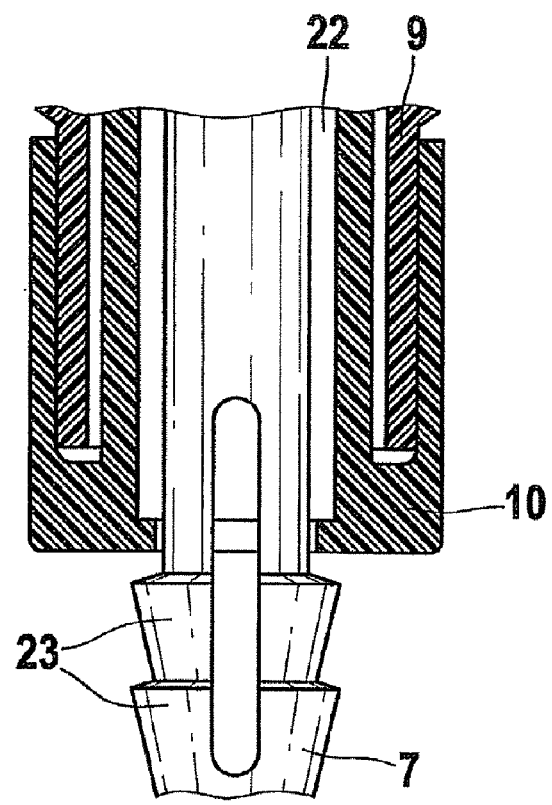
FIG. 6B is a sectional detail of a sterile protector of the puncture aid depicted in FIG. 6A.

FIG. 6B is an enlarged detail showing how the sterile protector protrudes from the housing in the unused state of the puncture aid. The sterile protector 7 fits in the opening 22 of the housing 9. The cap 10 for adjusting the puncture depth surrounds the housing 9 in the area shown. The sterile protector 7 has annular projections 23 which, before the use of the puncture aid, are positioned outside the opening 22 of the housing 9. To use the puncture aid, the sterile protector 7 is removed from the lancet tip and from the opening 22.

Figure 6C:
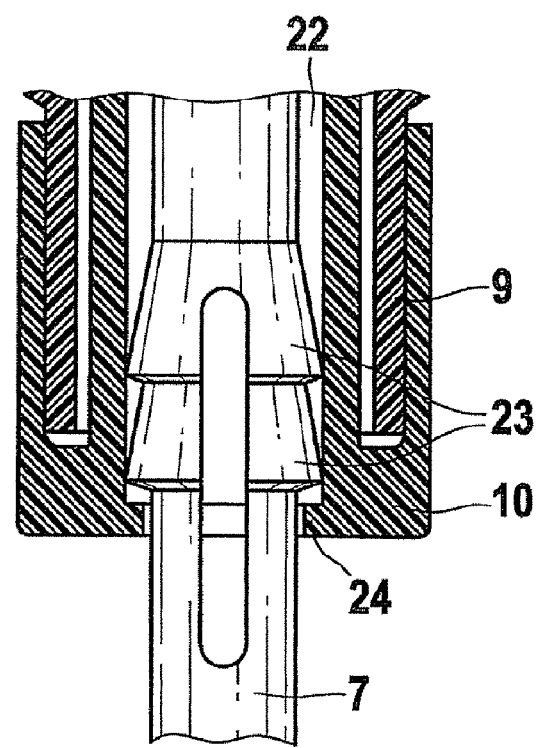
FIG. 6C is a sectional detail of a sterile protector inserted into the opening of the housing, after use of the puncture aid depicted in FIG. 6A.

After the use of the puncture aid, the sterile protector 7 can serve as a blocking element. To do so, the sterile protector 7 is turned round and pushed in the reverse direction back into the opening 22 of the housing 9. In this process, the projections 24 of the housing 9 lock behind the annular projections 23 of the sterile protector 7, so that the sterile protector 7 can no longer be pulled from the opening 22 of the housing 9, as is shown in FIG. 6C. In this position, the sterile protector prevents the bearing element 5 and the support surface 20 from executing a relative rotation movement with respect to one another, since no tool that could effect such a rotation movement can now be inserted from the outside into the opening 22 of the housing 9. The puncture aid is thus protected against being reused.

Figure 7A:
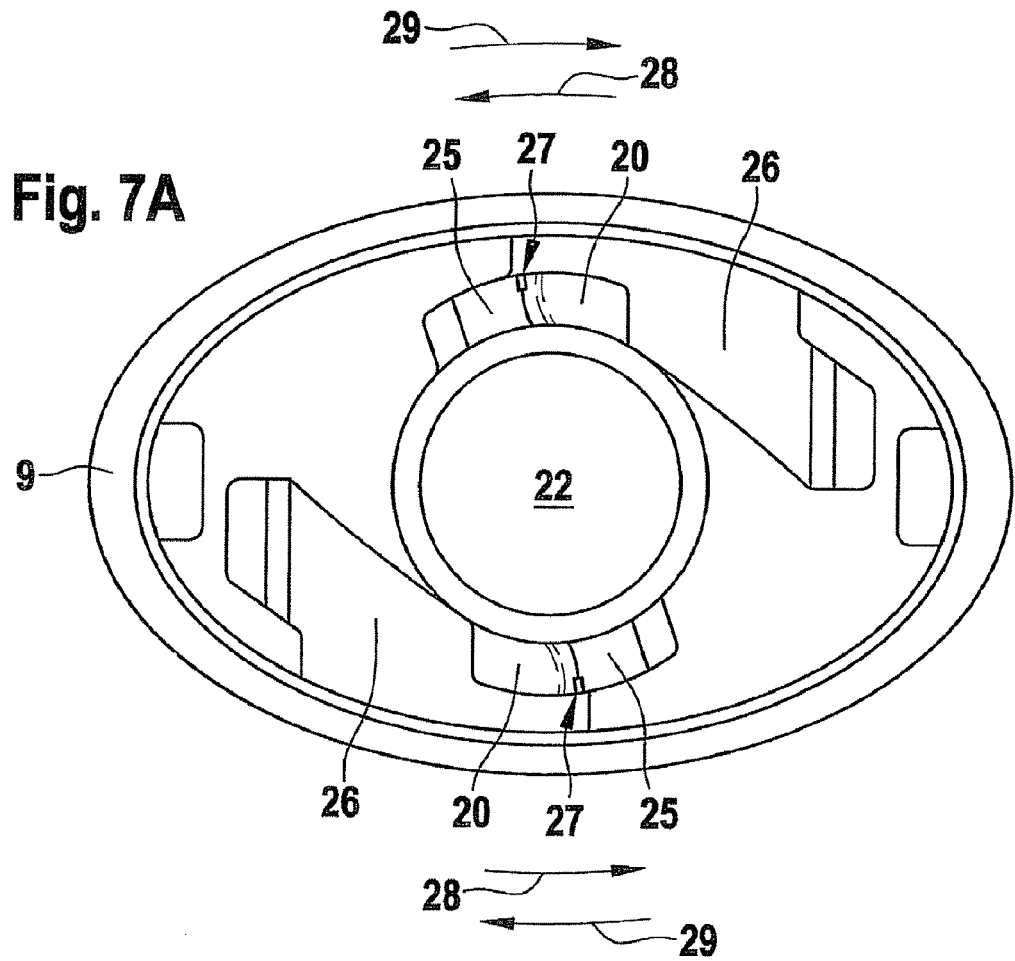
FIG. 7A is a plan view of the interior of the housing in a fifth embodiment of a puncture aid.

FIG. 7A shows a plan view of the interior of the housing in a fifth embodiment. Two support surfaces 20 for two bearing elements 5 can be seen in the housing 9. Moreover, the upper end of two guide grooves 25 is arranged alongside the support surfaces 20 and these extend along the opening 22 of the housing 9. When the bearing elements 5 (not shown in FIG. 7A) are rotated into the second position, they fall into these guide grooves 25, through which they slide during the falling movement.

The housing 9 also contains guide surfaces 26 which serve to guide the rotary drive elements of the trigger when the trigger is pressed in order to trigger the puncture process. The rotary drive elements then slide along these guide surfaces 26 and press against the bearing elements, as a result of which the rotational movement of the bearing elements relative to the support surfaces 20 is caused. Switch elements 27 are provided as blocking elements at the edge of the support surfaces 20. These switch elements 27 are designed to be movable in a first direction 28 so as to allow the respective bearing element of the lancet holder to pass during a relative rotation movement of the bearing element and the support surface 20 into the second position of the lancet holder. Movable in this context means that the switch element 27 can be folded or bent aside in this direction. In a second direction 29, the switch elements 27 are movable only as far as a blocking position in which the respective switch element 27 blocks the lancet holder (or the bearing elements) in such a way that it prevents a rotation movement back into the first position. The switch elements 27 accordingly serve as blocking elements. In the blocking position, the switch elements 27 are, for example, oriented perpendicularly with respect to the support surfaces 20. However, they can also assume any other position in which they block the return movement of the bearing elements to the first position onto the support surface.

Figure 7B:
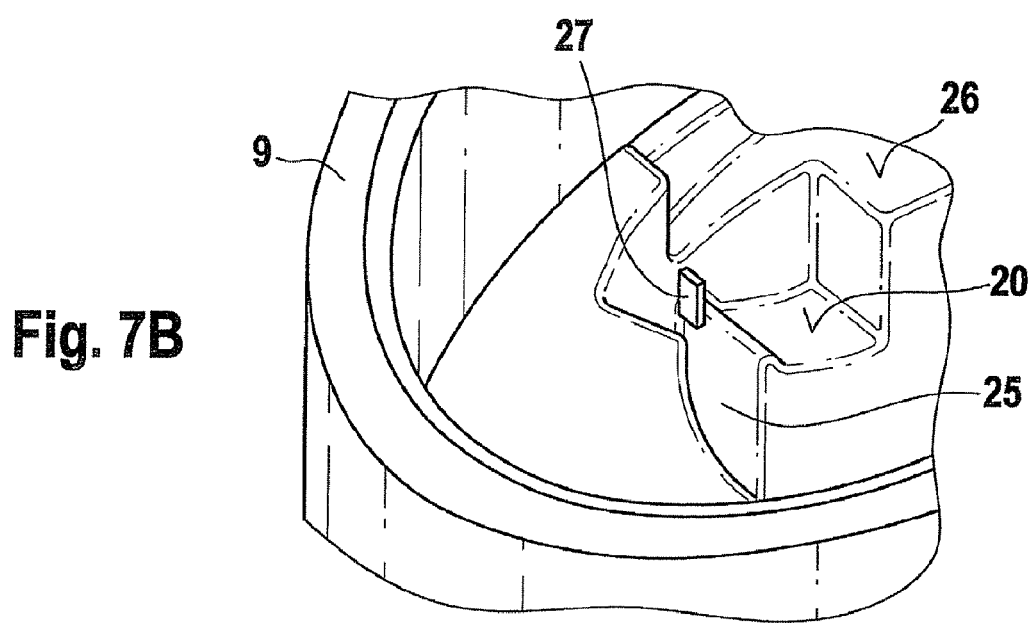
FIG. 7B is a sectional detail of the housing interior of the puncture aid depicted in FIG. 7A.

FIG. 7B is a perspective view of a detail of the housing interior of the puncture aid as depicted in FIG. 7A. A support surface 20, a switch element 27, a guide groove 25 and a guide surface 26 in the housing 9 can be seen in particular.

Figure 8A:
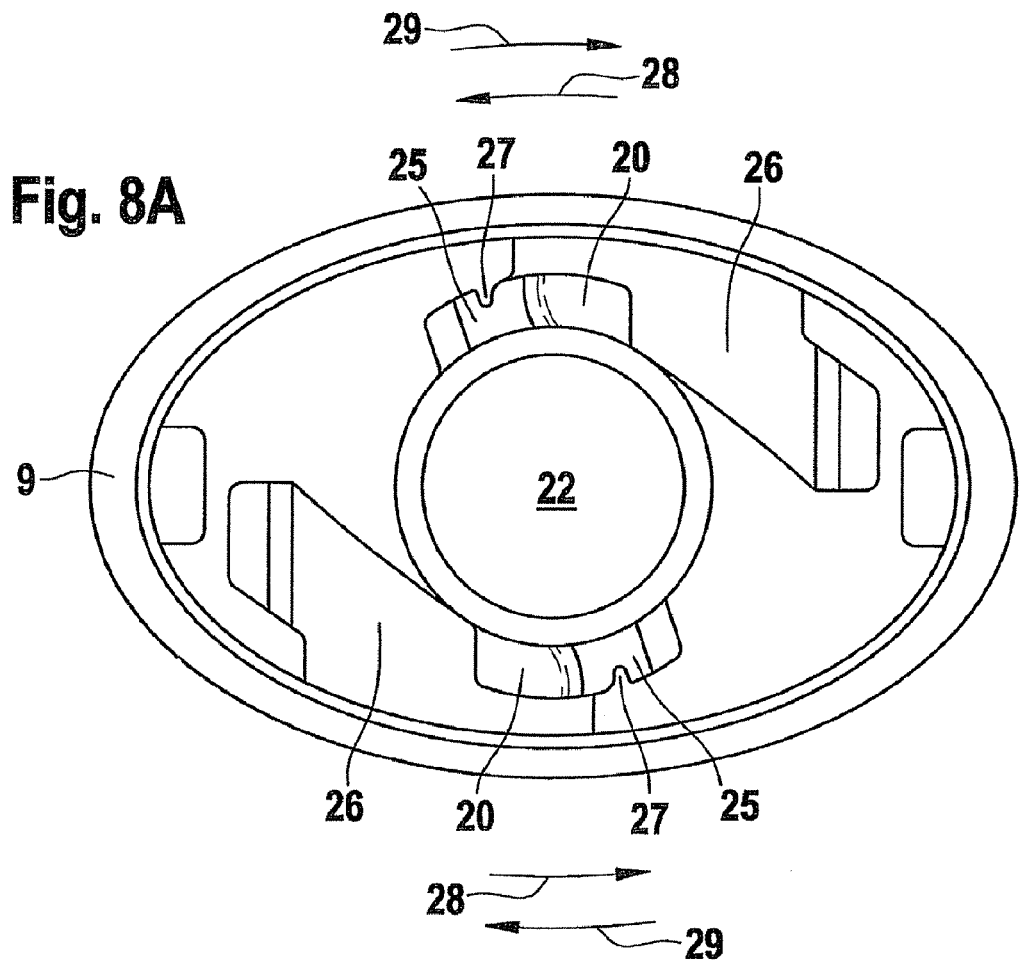
FIG. 8A is a plan view of the interior of the housing in a sixth embodiment of a puncture aid.

FIG. 8A shows a plan view of the interior of the housing in a sixth embodiment. This puncture aid has a housing 9 with two guide surfaces 26, two guide grooves 25, two support surfaces 20 and two switch elements 27. The mode of operation of the puncture aid corresponds to that described in respect of FIGS. 7A and 7B. The switch elements 27 provided as blocking elements are in this case arranged at another location in the housing 9. They are each located at the edge of a guide groove 25 alongside the support surface 20.

Figure 8B:
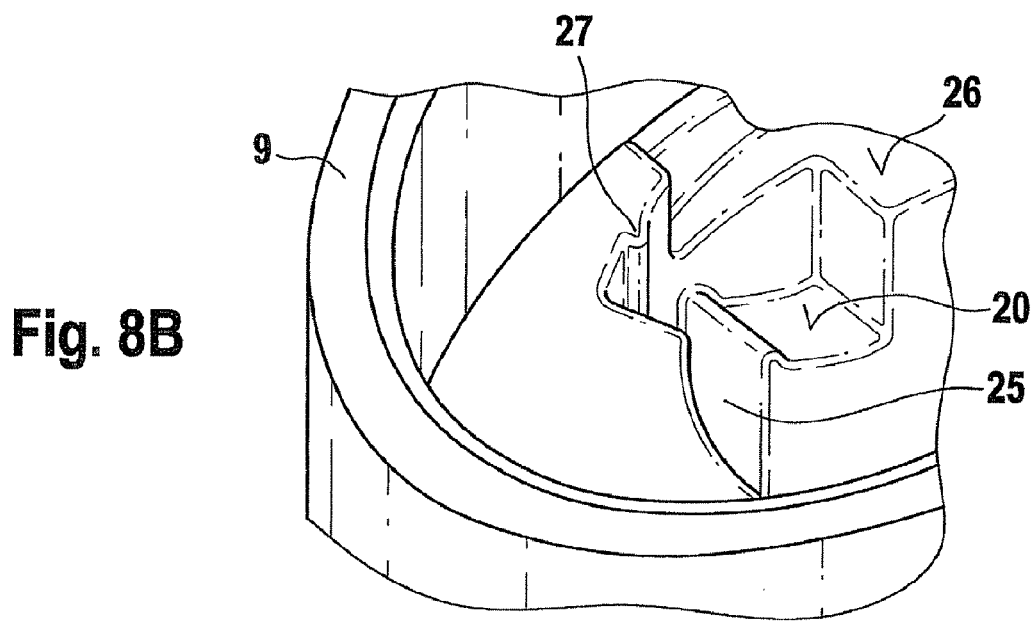
FIG. 8B is a sectional detail of the housing interior of the puncture aid depicted in FIG. 8A.

FIG. 8B is a perspective view of a detail of the hosing interior of the puncture aid as depicted in FIG. 8A. A guide surface 26, a support surface 20, a switch element 27 and a guide groove 25 in the housing 9 can be seen in particular.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMBERS 1 trigger unit or trigger
2 trigger button
3 small hooks, rotary drive elements, or drive elements
4 drive spring
5 bearing elements
6 lancet holder
7 sterile guard
8 return spring
9 housing
10 cap
11 hook or hook element
12 upper projections
13 axial direction
14 lower projections
15 recesses
16 housing openings
17 edge
18 lower hooks
19 upper hooks
20 support surfaces
21 projections
22 opening
23 annular projections
24 projections
25 guide grooves
26 guide surfaces
27 switch elements
28 first direction
29 second direction

What is claimed is:

1. A puncture aid, comprising:
a housing which has an opening and in which a lancet holder with a lancet is displaceably mounted, the lancet holder being connected to a spring element and having a bearing element, the housing having a support surface arranged such that the bearing element rests on the support surface in a first position of the lancet holder;
a trigger, actuation of which transfers the lancet holder to a second position by means of a rotation of the bearing element and the support surface with respect to one another, wherein the bearing element falls from the support surface in the second position of the lancet holder, during which, the spring element, tensioned prior to the falling movement, at least partially relaxes and moves the lancet holder relative to the housing, such that the tip of the lancet emerges from the opening of the housing; and
wherein, the puncture aid comprises a blocking element configured to block a second rotation of the bearing element and the support surface with respect to one another after the trigger has transferred the lancet holder to the second position, the second rotation comprising a return rotation of the bearing element and the support surface relative to one another from the second position to the first position, or the second rotation comprising a renewed rotation of the bearing element relative to the support surface from the first position to the second position in which the bearing element falls from the support surface, wherein the blocking element is positioned to block a movement path of the bearing element onto the support surface or to block access to the bearing element, whereby reuse of the puncture aid is prevented.

2. The puncture aid of claim 1, wherein the trigger executes a substantially linear movement when actuated, and the substantially linear movement is converted into the rotation of the bearing element and the support surface with respect to one another.

3. The puncture aid of claim 1, wherein the blocking element automatically blocks the second rotation of the bearing element and the support surface with respect to one another after the trigger has transferred the lancet holder to the second position.

4. The puncture aid of claim 1, wherein the blocking element comprises a rotary drive element which is pressed against the bearing element via a substantially linear movement of the trigger, which effects a rotation of the bearing element relative to the support surface, the trigger having a hook arranged such that, after the substantially linear movement of the trigger, a return movement of the trigger is prevented.

5. The puncture aid of claim 4, wherein after the substantially linear movement of the trigger, the hook hooks into a recess of the housing or behind a projection of the housing.

6. The puncture aid of claim 4, wherein during the substantially linear movement of the trigger, the hook slides over a ramp-shaped projection of the housing and, after the linear movement, hooks in behind the ramp-shaped projection.

7. The puncture aid of claim 4, wherein, before the puncture movement of the lancet is triggered, the hook hooks the trigger to the housing, thereby preventing detachment of the trigger from the housing.

8. The puncture aid of claim 4, wherein the trigger has at least two hooks, a first one of the hooks serving to hook the trigger in the housing before the puncture movement is triggered, and a second one of the hooks serving to hook the trigger in the housing after the substantially linear movement, whereby the return movement of the trigger is prevented.

9. The puncture aid of claim 1, wherein the blocking element comprises a sterile protector detachably connected to the lancet, the sterile protector having projections configured such that, after the puncture movement of the lancet, the sterile protector can be inserted as the blocking element into the opening of the housing, the sterile protector thereby hooking its projections in the opening and blocking the opening.

10. The puncture aid of claim 1, wherein the blocking element comprises a switch element which is movable in one direction to allow the lancet holder to pass during the rotation of the bearing element and the support surface with respect to one another from the first position to the second position and prevents a return rotation to the first position.

11. The puncture aid of claim 10, wherein the switch element is arranged at an edge of the support surface or on the lancet holder.

12. A puncture aid, comprising:
a housing having a support surface;
a lancet holder movably mounted in the housing and including a bearing element which rests on the support surface when the lancet holder is in a first position;
a trigger, movement of which causes the bearing element and the support surface to rotate relative to one another and the lancet holder to rotate to a second position in which the bearing element falls from the support surface;
a spring in engagement with the lancet holder and being tensioned prior to the lancet holder rotating to the second position, the spring at least partially relaxing when the lancet holder rotates to the second position and thereby moving the lancet holder in a puncturing direction; and
a blocking element configured to prevent a return rotation of the lancet holder to the first position or a renewed rotation of the lancet holder from the first position to the second position in which the bearing element falls from the support surface, wherein the blocking element is positioned to block a movement path of the bearing element onto the support surface or to block access to the bearing element, whereby reuse of the puncture aid is prevented.

13. The puncture aid of claim 12, wherein the movement of the trigger is substantially linear.

14. The puncture aid of claim 12, wherein the movement of the trigger is substantially linear and is converted into the rotational movement of the bearing element and the support surface relative to one another.

15. The puncture aid of claim 12, wherein the blocking element blocks the return rotation of the lancet holder to the first position after the movement of the trigger.

16. The puncture aid of claim 12, wherein the blocking element comprises a drive element which abuts the bearing element during the movement of the trigger, thereby effecting the rotation of the bearing element relative to the support surface.

17. The puncture aid of claim 16, wherein the drive element comprises a rotary drive element.

18. The puncture aid of claim 17, wherein, after the movement of the trigger, the drive element substantially occupies the position on the support surface that is occupied by the bearing element in the first position of the lancet holder.

19. The puncture aid of claim 18, wherein the trigger comprises a hook element that engages the housing and prevents a return movement of the trigger and which thereby prevents a return movement of the drive element.

20. The puncture aid of claim 12, wherein the trigger comprises a hook element that engages the housing and prevents a return movement of the trigger.

21. The puncture aid of claim 20, wherein the movement of the trigger causes the hook element to engage a recess or projection of the housing.

22. The puncture aid of claim 20, wherein during the movement of the trigger, the hook element slides over a ramp-shaped projection of the housing.

23. The puncture aid of claim 20, wherein the movement of the trigger is substantially linear.

24. The puncture aid of claim 20, wherein, before the movement of the lancet holder in the puncturing direction, the hook element hooks the trigger to the housing, thereby preventing detachment of the trigger from the housing.

25. The puncture aid of claim 20, wherein the trigger includes a second hook element, the second hook element hooking the trigger in the housing before the movement of the trigger.

26. The puncture aid of claim 12, wherein the blocking element comprises a sterile protector detachably connected to the lancet holder, the sterile protector having projections configured such that, after the movement of the lancet holder in the puncturing direction, the sterile protector can be manually inserted into the opening of the housing.

27. The puncture aid of claim 12, wherein the blocking element comprises a switch element which is movable in one direction to allow the lancet holder to pass during the rotation of the bearing element and the support surface relative to one another, the switch element preventing the return rotation of the lancet holder to the first position.

28. A puncture aid, comprising:
a housing defining a support surface;
a lancet holder movably mounted in the housing and having a bearing element that rests on the support surface when the lancet holder is in a first position;
a spring engaging the lancet holder;
the lancet holder being rotatable relative to the housing from the first position to a second position in which the bearing member is removed from the support surface, whereupon the spring advances the lancet holder in a puncturing direction; and
a blocking element configured to prevent a second rotation of the lancet holder, the second rotation comprising a return rotation of the lancet holder relative to the housing from the second position to the first position, or the second rotation comprising a renewed rotation of the lancet holder relative to the housing from the first position to the second position in which the bearing element falls from the support surface, wherein the blocking element is positioned to block a movement path of the bearing element onto the support surface or to block access to the bearing element, whereby reuse of the puncture aid is prevented.

29. The puncture aid of claim 28, further comprising a trigger connected to the housing, the trigger having a drive element that presses against the bearing element when the trigger is actuated, thereby causing the rotation of the lancet holder to the second position.

30. The puncture aid of claim 29, wherein the trigger moves in a substantially linear direction when actuated.

31. The puncture aid of claim 29, wherein the actuation of the trigger tensions the spring.

32. The puncture aid of claim 29, wherein the trigger comprises a hook element that connects to the housing during the actuation of the trigger, which prevents a return movement of the trigger and thereby prevents a return movement of the drive element.

33. The puncture aid of claim 32, wherein the drive element comprises the blocking element, further wherein, after the actuation of the trigger, the drive element substantially occupies the position on the support surface that is occupied by the bearing element when the lancet holder is in the first position, the drive element thereby blocking return of the lancet holder to the first position.

34. The puncture aid of claim 28, wherein the blocking element comprises a removable sterile protector connected to the lancet holder, the sterile protector being insertable in the puncture aid after use to prevent reuse of the puncture aid.

35. The puncture aid of claim 34, wherein the sterile protector is insertable into the puncture aid after use in an orientation substantially inverted from its orientation prior to use of the puncture aid.

36. The puncture aid of claim 28, wherein the blocking element comprises a switch element which allows the lancet holder to move from the first position to the second position but blocks a return movement of the lancet holder from the second position to the first position.

37. The puncture aid of claim 36, wherein the switch element is movable in a first direction to allow the bearing element to pass during movement of the lancet holder from the first position to the second position.

* * * * *